(12) United States Patent  (10) Patent No.: US 7,488,199 B2
Gonzalez  (45) Date of Patent: Feb. 10, 2009

(54) BUNDLING APPARATUS FOR ELECTRICAL CABLES

(75) Inventor: David Gonzalez, Apollo Beach, FL (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/620,087

(22) Filed: Jan. 5, 2007

(65) Prior Publication Data

US 2008/0165522 A1     Jul. 10, 2008

(51) Int. Cl.
*H01R 11/00* (2006.01)
(52) U.S. Cl. .................................... 439/502; 174/136
(58) Field of Classification Search ................ 174/135, 174/136, 134, 132; 439/502, 500
See application file for complete search history.

(56) References Cited

U.S. PATENT DOCUMENTS

| 2,494,285 | A | * | 1/1950 | Clapp ........................... 174/42 |
| 3,716,733 | A | * | 2/1973 | Keith et al. ..................... 310/71 |
| 5,435,871 | A | * | 7/1995 | Streit ............................ 156/201 |
| 6,674,005 | B2 | * | 1/2004 | Yagi et al. .................... 174/72 A |
| 6,826,837 | B2 | * | 12/2004 | Todd ............................. 30/210 |
| 6,901,627 | B2 | * | 6/2005 | Uchida ......................... 16/2.1 |

OTHER PUBLICATIONS

Web-page print-out for Niedax-Kleinhuis USA, Inc. http://www.kleinhuis.com/.
Web-page print-out for "Cableyoyo™" from Cableorganizer.com, website address: http://cableorganizer.com/cable-yoyo/?engine+overture&KW=cable.
Web-page print-out for "Telescoping Lacer System" from Middle Atlantic Products, Inc., website address: http://www.middleatlantic.com/dcm/access/cm.htm.
"Networking and Protecting" manual, obtained from www.htamericas.com/cable_management.asp.
Web Article: "Multiple Use Cable Control" obtained from website address: http://www.nwraleigh.com/cablecontrol.html.
Web-page print-out for Northwire, Inc. Technical Cable, website address: http://www.northwire.com/custom/refractile.
Web-page print-out of XPCGear, website address: http://www.xpcgear.com/retractables.html?gclid+CPjUgvy8zYYCF.
Web-page print-out from Amazon.com. website address: http://www.amazon.com/Cord-Clips-Self-Adhesive-Backing-Cavity.
Web-page print-out from CABLEscience™, website address: http://www.cablescience.com/idex.html.
Web-page print-out for "Wire Loom", website address: http://cableorganizer.com/wire-loom/colored.html.
Web-page print-out for Cirris, website address: http://www.cirris.com/adapters/easywire/index.html.

* cited by examiner

*Primary Examiner*—Phuong K Dinh
(74) *Attorney, Agent, or Firm*—Andrus, Sceales, Starke & Sawall, LLP

(57) ABSTRACT

A bundling apparatus for the organization of electrical wires. The bundling apparatus comprising a body with a first end and a second end, the body being movable from an extended position to a compressed position. The body holding the electrical wires together when the bundling apparatus is in the extended position and the electrical wires being movable when the bundling apparatus is in the compressed position.

19 Claims, 5 Drawing Sheets

BUNDLING APPARATUS FOR ELECTRICAL CABLES

FIELD OF THE DISCLOSURE

The present disclosure relates to the field of peripheral accessories for use with electronic devices. Specifically, the present disclosure relates to an apparatus for organizing and maintaining the organization of a plurality of electrical cords that are associated with an electronic device, such as a medical device.

BACKGROUND OF THE DISCLOSURE

Electronic devices perform many useful and desirable functions that improve our lives everyday, whether it is our recreation, our profession, or even our health. Recreationally, these electronic devices include, but are not limited to, computers, home entertainment systems, televisions, stereos, and video game equipment. Professionally, electronic devices include computers, fax machines, scanners, photocopiers, network servers and many other devices. In the healthcare field, electronic patient monitoring and diagnostic systems are now a common component of the treatment and care that a patient receives at a medical care facility. All of these electronic devices have a common feature in that they require multiple power and/or data cables that extend from each of these devices to either other devices, or an external source of data, such as when a patient is hooked up to a patient monitoring system. One problem associated with the use of many electronic devices is that the cables extending from these devices commonly become tangled. Tangled cables not only may harm power supplies or data transmission, but the tangled cables and cords also make the full extension of the cords difficult. Furthermore, electronic data cords that are tangled and/or not orderly positioned are more likely to be damaged and/or pulled out of a connection with an associated electronic device.

Systems have been developed to address these concerns. One of these solutions is the use of a retractile cord, such as a telephone cord, where the cord itself is shaped such that the cord may be extended relatively easily, however the cord retracts upon itself to form a tightly wound coil that is more resistant to kinking and tangling. Yet another alternative solution is the use of a mechanical and/or spring loaded retracting case within which the electrical wires are attached, such that the electrical wires may be extended out for use, and after use, may be retracted back into the case. An alternative solution has been to use individual ties, clips, or pieces of tape to bundle the electrical wires together such that all of the electrical wires are held together in a single movable bundle. Alternatively, bundle ties exist that wind around a plurality of electrical wires to hold the wires together. Another form of bundler includes a plastic sleeve or cover, within which the electrical wires are disposed and held together.

The electrical wire organization solutions described above are all limited in their effectiveness as each of the systems make it difficult to switch between a condition in which the electrical wires are bundled and a condition in which the electrical wires are free to be moved individually. Furthermore, these prior art bundlers are limited in that it is difficult to change the electrical wires that are bundled together, such as in the event of the need to replace one or more of the electrical wires, or the addition of a new electrical wire to the bundle. Bundlers known in the art make it difficult to access the individual wires from the bundle when it is desired to use a wire individually in a different direction than the other electrical wires in the bundle. Furthermore, while some of the bundlers in the prior art retract the power cord into the bundler, or the electrical wire itself retracts upon itself, none of the current bundlers themselves are retractable such that the length bundler is extendable to bundle any desired length of the electrical wire.

Therefore, it is desirable in the field of electronic devices for a bundling apparatus that holds electrical wires together, but is retractable or movable to allow access or movement to individual electrical wires during use. Furthermore, a bundling apparatus that is removably attachable to the electrical wires is desired such that the bundling apparatus need only be used when wire bundling is needed. Furthermore, it is desirable for the bundling apparatus to include a mechanism by which the bundling apparatus is movable from an extended position, wherein the electrical wires are held in a bundle, and a contracted position wherein the electrical wires are free to be individually moved.

In the healthcare field, a patient monitoring device, such as patient vital sign monitors (VSM), monitors basic psychological parameters of a patient. Patient monitoring devices require a number of electrical wires to be attached to the patient, either in the form of electrodes which are attached to the skin of the patient, or to an alternative physiological parameter transducer, such as a pressure sensor in a blood pressure monitoring cuff, or an $SPO_2$ sensor attached to the patient's ear or finger. Therefore, a patient monitoring system requires a plurality of wires to be attached to the patient. These wires have a high likelihood of being tangled or damaged during the transport of the patient monitoring system to the location where it is to be used. Therefore, it is desirable to maintain the electrical wires in a bundled condition during the transport of the patient monitoring system. Alternatively, it is desirable to have the electrical wires to be partially bundled during use of the patient monitoring system, such that the electrical wires are bundled until the are at a position that is close to the patient. Once the monitoring system is in position, the electrical wires may be branched out individually to the specific locations on the patient from which the desired psychological data is acquired.

SUMMARY OF THE DISCLOSURE

A bundling apparatus for holding electrical wires in a bundle. The bundling apparatus includes a body and a first end and a second end, the first end and the second end being disposed for connection to a plurality of electrical wires.

In an embodiment of the bundling apparatus, the bundling apparatus is used for the organization of a plurality of electrical wires used with a patient monitoring system.

In a further embodiment, the bundling apparatus comprises a first fastener on the first end of the body, the first fastener being used to attach the body of the bundling apparatus to a plurality of electrical wires.

In a still further embodiment, the body of the bundling apparatus is biased to an extended position, and the bundling apparatus comprises a second fastener on the second end of the body for fastening the body in a compressed position.

In a still further embodiment, the body of the bundling apparatus is biased to be in an compressed position, and a second fastener on the second end of the body fastens to the plurality of electrical wire such that the body of the bundling apparatus is held in an extended position.

DETAILED DESCRIPTION

Figure 1:
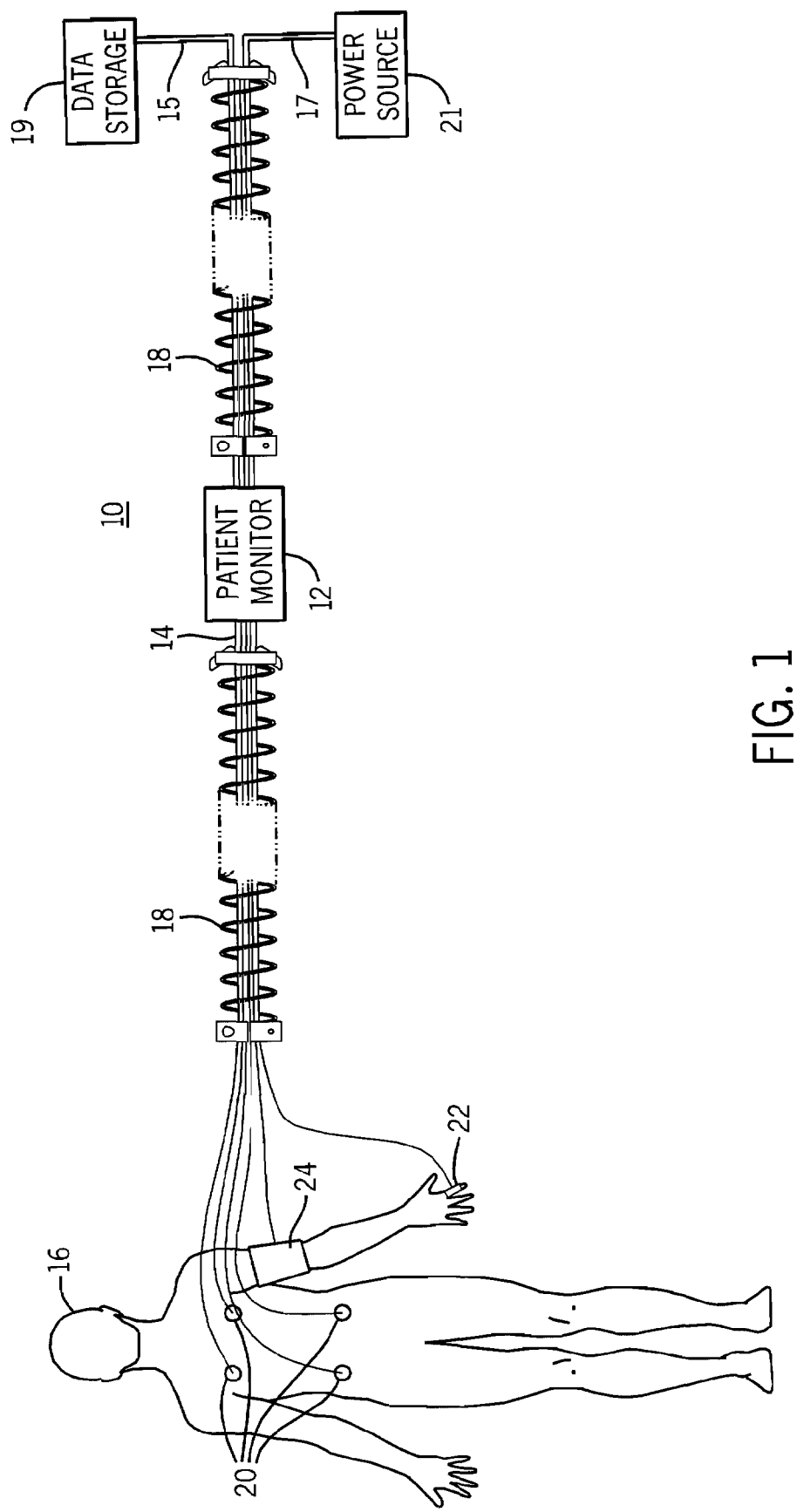
FIG. 1 is a schematic diagram depicting an embodiment of a bundling apparatus in use in a clinical setting.

FIG. 1 depicts a patient monitoring system 10. The patient monitoring system 10 may comprise a patient monitor 12 positioned to interact with a patient 16. Between the patient 16 and the patient monitor 12 extends a plurality of data collection lead wires 14. The data collection lead wires 14 are held together by a bundling apparatus 18. The plurality of data collection lead wires 14 may comprise lead wires that extend to ECG electrodes 20, a finger probe 22 of an $SPO_2$ monitor, or a non-invasive blood pressure cuff 24; however, these physiological parameter transducers are in no way meant to be limiting on the types of transducers that may be attached to the plurality of data collection lead wires 14 depicted in FIG. 1. The bundling apparatus 18 that bundles the plurality of data collection lead wires 14 may extend from a point close to the patient monitor 12 to a point close to the patient 16 wherefrom the plurality of data collection lead wires 14 extend to the different transducers attached to the patient 16.

The patient monitor 12 may also comprise data transmission cables 15 that extend from the patient monitor 12 to some type of remote data storage 19. The remote data storage 19 may be a hospital information network server, or may be another form of centralized computer, such as a computer workstation in the room with the patient 16. Furthermore, the patient monitor 12 may comprise a power cord 17 that extends from the patient monitor 12 to a power source 21, such as a wall outlet. A bundling apparatus 18 may be used to hold cords such as the data transmission cable 15 and the power cord 17. The bundling apparatus 18 may hold these cords together for a specified distance until the cords split to be directed to their individual destinations. The depiction of a bundling apparatus 18 in use with a patient monitoring system 10 in FIG. 1 is not intended to be limiting upon the type of electronic devices with which the bundling apparatus 18 may be used. Alternatively, the bundling apparatus 18 may be used with any other type of electronic device; specifically, devices for recreational or professional use that may include, but are not limited to, personal computers, network servers, TVs, stereo equipment, video equipment.

Figure 2:
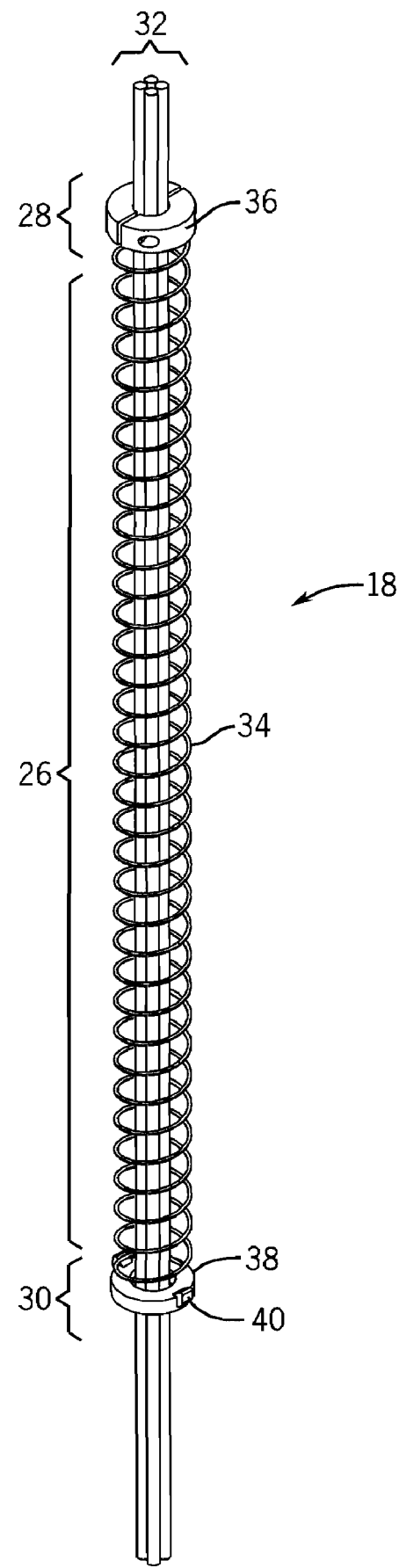
FIG. 2 is an embodiment of the bundling apparatus, wherein the body comprises a spring that extends between the first end and the second end.

FIG. 2 depicts an embodiment of a bundling apparatus 18. The bundling apparatus 18 comprises a body 26 with a first end 28 and a second end 30. A plurality of electrical wires 32 are disposed within the bundling apparatus 18. Typically, the first end 28 may be connected at a location proximal to the electronic device to which the plurality of electrical wires 32 are connected in comparison to the second end 30; however, in embodiments of the bundling apparatus 18, this orientation may be switched.

The first end 28 comprises a first fastener 36 for attaching the first end 28 of the bundling apparatus 18 to the plurality of electrical wires 32. The first fastener 36 may comprise any suitable type of fastener for fastening a structure around another structure. In a merely exemplary list, the first fastener 36 may comprise a clam shell style hinged fastener, a hook and loop fastener, a cable tie style plastic fastener, a shoestring style fastener, or a clamp style fastener as depicted in FIG. 2. The first fastener 36 serves to securely attach the first end 28 of the bundling apparatus 18 to the plurality of electrical wires 32.

A body 26 of the bundling apparatus 18 extends away from the first end 28. In the embodiment of FIG. 2, the body 26 may comprise a spring 34. The spring 34 may be made of metal or any other suitable material. In a further embodiment, the spring 34 may be covered with a plastic, rubber, or cloth material, such that the body 26 comprises a closed cylinder (not depicted), yet still maintaining the properties of the spring 34 underneath the covering. The spring 34 of the body 26 may be a spring that is biased to a compressed position, such that a mechanical force is required to extend the spring 34 of the body 26 away from the first end 28. In the embodiment of FIG. 2, the second end 30 comprises a fastener 38, the fastener 38 serving to hold the body 26 and the second end 30 in an extended position, such that the bundling apparatus 18 covers an extended length of the electrical wires 32. The second fastener 38 of the second end 30 may comprise a clip or a clamp such that the clip or clamp mechanically contacts the plurality of electrical wires 32 and holds the body 26 and the second end 30 in an extended position. Upon release of the fastener 38, the bias force of the spring retracts the spring 24 to a compressed position.

In an alternative embodiment, the second fastener 38 may comprise a weighted second end 30, such that when the plurality of electrical wires are held in a vertical position with the first end 28 being above the second end 30 the force of gravity pulls the second end 30 to an extended position. In the embodiment of FIG. 2, the plurality of electrical wires 32 must be oriented in a vertical or nearly vertical orientation. However, this embodiment may be used as a storage device for the plurality of electrical wires 32 when the wires 32 are not in use. In the embodiment of FIG. 2, a person using the wires 32 will pull on the wires 32, directing the wires towards a target destination, such as a patient 16. The force of pulling on the wires 32 in different directions or in an orientation away from vertical will retract the bundling apparatus 18, and allow for the free movement of the wires 32. Once the tension is removed from the wires 32, as in when the wires 32 are disconnected from the patient 16, the wires 32 may return to a generally vertical orientation and the weighted second end 30 will hold the wires together and keep the wires safe from damage or tangling during transportation or storage.

In an alternative embodiment, the spring 34 may be biased to an extended position, wherein a mechanical force is needed to compress the spring to place the body 26 in a compressed position. The second end 30 may comprise a third fastener 40, the third fastener 40 being disposed to hold the body 26 and spring 34 in a compressed position. As depicted in FIG. 2, the third fastener 40 may comprise a latch that attaches to the first end 28 to hold the second end in a position attached to the first end 28 to hold the body 26 in a compressed position. The third fastener 40 may comprise a variety of latches to maintain the mechanically compressed body 26 in a compressed position. The third fastener 40 may comprise a latch that attaches the second end 30 to first end 28, such that the second end 30 and the first end 28 are held in a communicable position. The third fastener 40 may further comprise a clamp (not depicted) such that when the body 26 is in a compressed position the clamp may be closed on the plurality of electrical wires 32 and the spring 34 of the body 26 may be held in a compressed position.

The third fastener 40 may further comprise a friction based fastener (not depicted). If the third fastener 40 is a friction based fastener, the second end 30 comprises an opening large enough to be able to pass the second end 30 over the attached first end. The flexible body 26 is bent back on itself, thereby compressing the body. The second end 30, being pulled to a position above the first end 28, may attach to the plurality of wires 32 by the fastener 40. Alternatively, the friction between the second end 30 and the wires 32 and the friction between the body 26 doubled back upon itself, holds the body in the compressed position.

Figure 3:
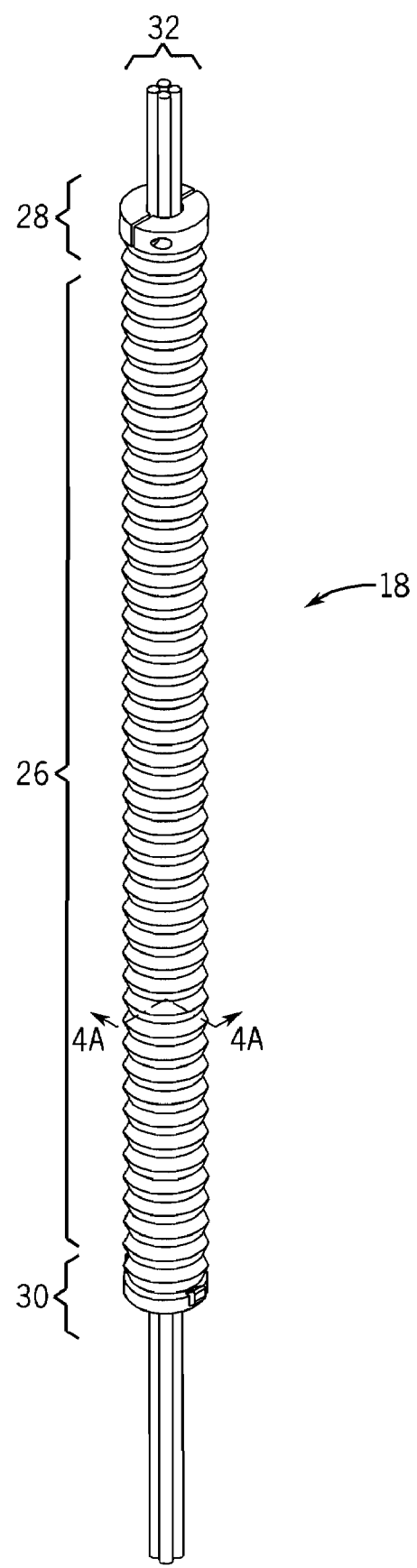
FIG. 3 depicts a second embodiment of the bundling apparatus wherein the body comprises corrugated material.

FIG. 3 depicts an embodiment of a bundling apparatus 18 comprising a first end 28, a body 26 and a second end 30. The body 26 comprises a corrugated material. The corrugated material may be a metal or a plastic material. In the embodiment shown, the body 26 may be disposed such that the body 26 may be compressed and the corrugated material holds the body 26 in a compressed position and when the body 26 is extended, the corrugated material holds the body 26 in an extended position. Alternatively, the first end 28 and the second end 30 may comprise fasteners (not depicted) such as the first fastener 36, second fastener 38, and third fastener 40 as depicted in FIG. 2. The fasteners may hold the first end 28 and the second end 30 in contact with the plurality of electrical wires 32, such that the bundling apparatus 18 is held in the desired position for bundling the plurality of electrical wires 32. The fasteners may be used to hold the bundling apparatus 18 in either a compressed or an extended position.

Figure 4A:
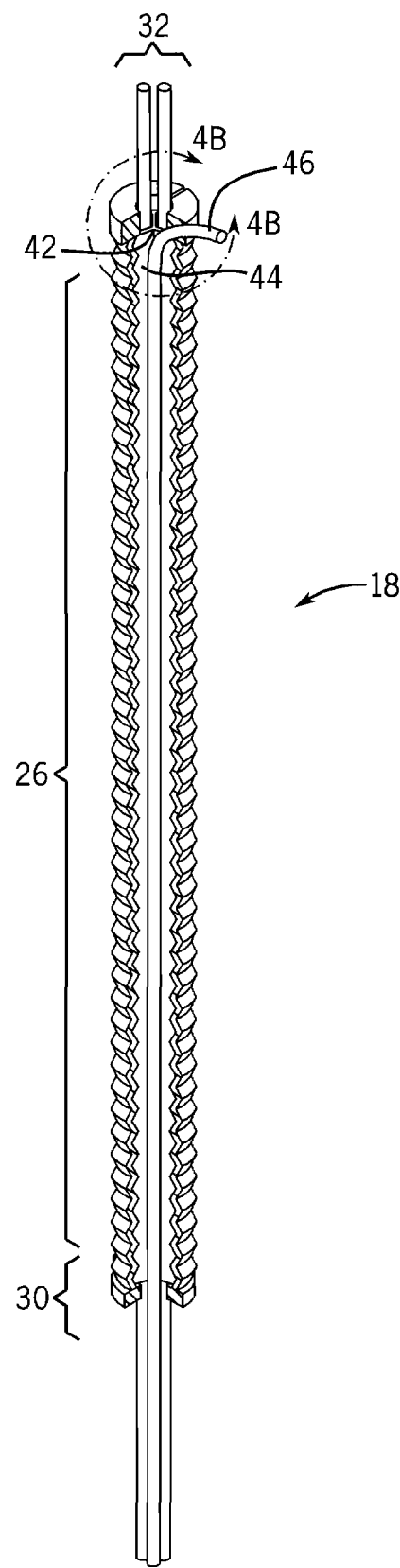
FIG. 4A depicts a cut away view of an embodiment of a bundling apparatus along line 4A-4A of the FIG. 3.
Figure 4B:
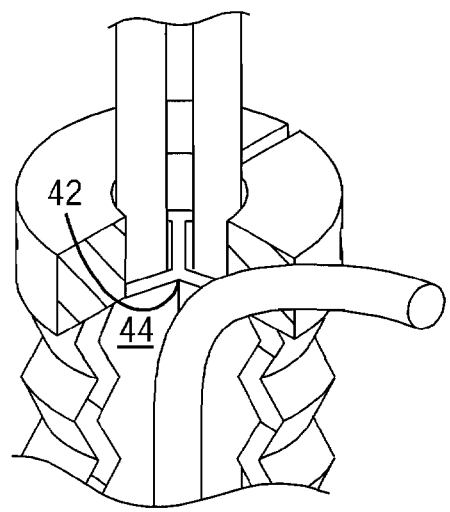
FIG. 4B depicts a magnified partial sectional view of the embodiment in FIG. 4A cut along 4B-4B.

FIG. 4A depicts a cut away view of the bundling apparatus 18 as depicted in FIG. 3 cut along lines 4A-4A. The cut away view in FIG. 4 depicts an embodiment of the bundling apparatus 18 wherein a separator 42 is disposed within the body 26 of the bundling apparatus 18. FIG. 4B depicts a magnified partial sectional view of the embodiment depicted in FIG. 4A cut along line 4B-4B. The separator 42 divides the body 26 of the bundling apparatus 18 into a number of compartments 44, such as the three compartments 44 as depicted in FIG. 4B; however, the separator 42 may divide the body 26 into any number of compartments 44.

In the operation of the embodiment depicted in FIG. 4A, one electrical wire 46 may be disposed within each of the compartments 44 defined by the separator 42. The bundling apparatus 18 of FIG. 4 reduces any twisting or tangling of the electrical wires 46 by keeping the electrical wires 32 bundled together within the bundling apparatus 18, and keeping the individual wires 46 separate from each other. Additionally, when the bundling apparatus 18 is in a contracted position, the plurality of wires 32 are free to be moved individually, and may become entangled during use. This may present a problem when it is desired to move the bundling apparatus 18 to an extended position, to rebundle the plurality of electrical wires 32 as the entangled wires may impair the functionality of the bundling apparatus 18 or contradict its use. As the body 26 of bundling apparatus is extended from the compressed position to the extended position, the separator 42 disposed within the body 26 serves to separate the individual wires 46 and to untangle them as they are rebundled by the bundling apparatus 18.

Figure 5:
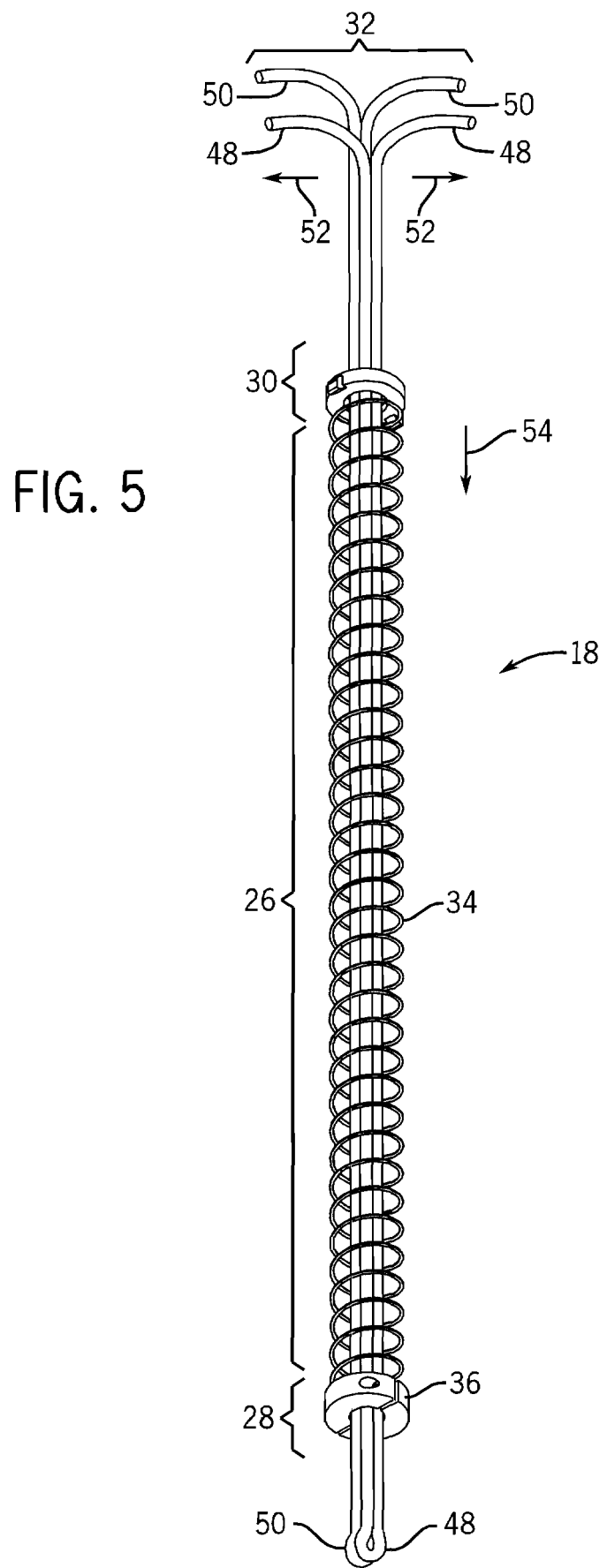
FIG. 5 depicts an alternative embodiment of a bundling apparatus.

FIG. 5 depicts an alternative embodiment of the bundling apparatus 18. The bundling apparatus 18 comprises a first end 28, a body 26, and a second end 30; however, the plurality of wires 32 are inserted into the bundling apparatus 18 through the second end 30, extend through the body 26 and out the first end 28 where the plurality of electrical wires 32 are looped and fed back through the bundling apparatus 18 such that they extend back out the second end 30. As depicted in FIG. 5, the plurality of wires 32 comprises individual wires 48 and 50; however, any number of wires may comprise the plurality of wires 32. In operation, the first end 28 comprises a fastener 36 such that the first end 28 is securely attached to wires 48 and 50. The body 26 further comprises a spring 34 that is biased to an extended position, such that the body 26 is normally extended, and wires 48 and 50 are bundled together. If one or more of the plurality of wires 32 are needed to be extended to a patient, or connect to another electrical device, the plurality of electrical wires 32 are pulled to extend the wires to the desired location. The separative force applied to the two ends of wires 48 and 50 along arrows 52 will force the end of wires 48 and 50 apart; which in turn, forces the second end 30 of the bundling apparatus downwards in the direction of arrow 54. The downward force compresses the body 26 thus freeing more of the electrical wire 48 and 50 to be independently maneuvered to connect the wires to a desired target such as a patient or another electrical device. When the electrical wires 48 and 50 are done being used, the electrical wires 48 and 50 are detached and the separative force 52 is relaxed such that the spring 34 once again extends the body 26 back out to its extended position. The bundling apparatus 18 then rebundles the electrical wires 48 and 50, such that the wires are not tangled and are protected from damage while the electronic device is not being used.

Embodiments of the bundling apparatus present the advantage of being able to manage a plurality of electrical wires for data cables as a single bundle of electrical wires or data cables. This allows a user or clinician the ability to easily store, and/or move the plurality of electrical wires or data cables. Further embodiments of the disclosed bundling apparatus allow the user or clinician the further ability to access and move an individual cable from the set of bundled cables. Alternatively, the user or clinician has the ability to add or remove cables from the bundling apparatus.

Embodiments of the bundling apparatus further present the advantage of extending to maintain the wires for data cables bundled together, and compressing to allow the free movement of the wires or data cables. Alternatively, embodiments of the bundling apparatus present the advantage of separating the wires or data cables into individual compartments in the bundling apparatus such that upon the extension of the bundling apparatus to bundle the wires or data cables, the wires or data cables are untangled and straightened before being bundled.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A bundling apparatus for the organization of a plurality of electrical wires, the bundling apparatus comprising:
   a variable length body with a first end and a second end, the body being repeatedly adjustable between an extended position and compressed position and formed primarily for easy elastic longitudinal stretchability;
   a first fastener connected to the body at the first end, the first fastener fastening the first end of the body to the plurality of electrical wires; and a second fastener connected to the body at the second end, the second fastener fastening the second end of the body to the plurality of electrical wires, the second end being movable with respect to the plurality of wires between the extended position and the compressed position;

wherein when the body is in the compressed position, a first portion of each of the plurality of electrical wires are held together within the body and a second portion of each of the plurality of wires are outside the body and freely movable relative to each other.

2. The bundling apparatus of claim 1, further comprising a separator within the body, the separator being connected to the first end and the second end, the separator defining a plurality of compartments within the body.

3. The bundling apparatus of claim 1, wherein the body is disposed such that the plurality of wires enter the body through the second end, the body is attached to the wires at the first end, and the wires exit the body through the second end.

4. The bundling apparatus of claim 1, wherein the body comprises a corrugated material.

5. The bundling apparatus of claim 1, wherein the body comprises a spring.

6. The bundling apparatus of claim 5, where in the spring is biased to maintain the body in an extended position, and the second fastener fastens the body to the plurality of wires in a compressed position.

7. The bundling apparatus of claim 6, wherein the first fastener is a clamp.

8. A bundling apparatus for the organization of a plurality of data collection lead wires used with a patient monitoring system, the bundling apparatus comprising:

a body with a cylindrical shape having a first end and a second end, the body being movable from a compressed position to an extended position and formed primarily for easy elastic longitudinal stretchability;

a first fastener connected to the first end, the first fastener disposed to attach the body to the plurality of data collection wires;

a second fastener connected to the second end, the second fastener disposed to attach the body to the plurality of data collection lead wires; and a divider disposed within the body, the divider being connected to the first end and the second end of the body, and the divider defining a plurality of compartments within the body;

wherein the plurality of data collection lead wires are disposed within the body with at least one lead wire of the plurality of data collection lead wires disposed within each compartment of the body, and when the body is in the extended position, the wires are held together.

9. The bundling apparatus of claim 8 wherein the body is held in a compressed position by moving the second end over the first end and attaching the second end to the plurality of data collection lead wires at a position above the first end.

10. A bundling apparatus for the organization of a plurality of electrical wires, the bundling apparatus comprising:

a variable length body having a first end and a second end connected by a spring, the body being repeatably movable between a compressed position and an extended position; and formed primarily for easy elastic longitudinal stretchability;

a first fastener connected to the first end, the first fastener attaching the first end of the body to the plurality of electrical wires; and a second fastener connected to the second end, the second fastener attaching the second end of the body to the plurality of electrical wires to maintain the body in the compressed position or the extended position.

11. The bundling apparatus of claim 10, wherein the body comprises a corrugated material.

12. The bundling apparatus of claim 11 the second fastener attaches to the plurality of data collection lead wires at a point above the first end, thereby holding the body in a compressed position.

13. The bundling apparatus of claim 10, wherein the body is biased to maintain the body in the extended position and the second fastener is operable to fasten the body in the compressed position.

14. The bundling apparatus of claim 13, wherein the first fastener is a clamp.

15. The bundling apparatus of claim 14, wherein the second fastener is a latch that latches to the first end.

16. The bundling apparatus of claim 13, further comprising a separator within the body, the separator being connected to the first end and the second end, the separator defining a plurality of compartments within the body.

17. The bundling apparatus of claim 16, wherein the body is attached to the plurality of data collection lead wires at the first end, and the wires enter and exit the body through the second end.

18. The bundling apparatus of claim 17, wherein tension on the plurality of data collection lead wires compresses the body.

19. A bundling apparatus for the organization of a plurality of electrical wires, the bundling apparatus comprising:

a variable length body having a first end and a second end, the body being repeatably movable between a compressed position and an extended position; and formed primarily for easy elastic longitudinal strethchability;

a first fastener connected to the first end, the first fastener attaching the first end of the body to the plurality of electrical wires; and a weighed member connected to the second end such that when the first end is fastened to the plurality of electrical wires at a position above the second end, the body will be held in a extended position be the force of gravity.

* * * * *